United States Patent
Reid et al.

(10) Patent No.: US 9,348,001 B2
(45) Date of Patent: May 24, 2016

(54) METHOD AND SYSTEM FOR DETECTING SURFACE FEATURES ON TURBINE COMPONENTS

(71) Applicant: General Electric Company, Schenectady, NY (US)

(72) Inventors: Thomas Robert Reid, Greenville, SC (US); Paul Stephen Dimascio, Greer, SC (US); Jonathan Matthew Lomas, Simpsonville, SC (US)

(73) Assignee: General Electric Company, Schenectady, NY (US)

( * ) Notice: Subject to any disclaimer, the term of this patent is extended or adjusted under 35 U.S.C. 154(b) by 164 days.

(21) Appl. No.: 14/058,513

(22) Filed: Oct. 21, 2013

(65) Prior Publication Data

US 2015/0107341 A1  Apr. 23, 2015

(51) Int. Cl.
*G01M 15/14* (2006.01)
*G01R 33/038* (2006.01)
*G01N 27/90* (2006.01)

(52) U.S. Cl.
CPC ............. *G01R 33/038* (2013.01); *G01N 27/90* (2013.01)

(58) Field of Classification Search
CPC ..... G01M 15/14; G01N 27/90; G01N 21/956; G01R 33/038; F01D 5/005; F01D 5/288; F05D 2230/90; G01B 11/002; G01B 11/24; G05B 2219/45147
USPC .................................................. 73/112.01
See application file for complete search history.

(56) References Cited

U.S. PATENT DOCUMENTS

| | | | | |
|---|---|---|---|---|
| 4,040,748 A | * | 8/1977 | Belleson | G01B 11/002 356/398 |
| 5,670,879 A | * | 9/1997 | Zombo | G01N 27/9013 324/227 |
| 6,380,512 B1 | | 4/2002 | Emer | |
| 6,414,480 B1 | * | 7/2002 | Traxler | B82Y 15/00 324/202 |
| 6,606,528 B1 | * | 8/2003 | Hagmeier | G05B 19/4097 345/420 |
| 6,723,951 B1 | | 4/2004 | McGraw | |
| 6,909,800 B2 | | 6/2005 | Vaidyanathan | |
| 6,910,278 B2 | * | 6/2005 | Holder | B23P 6/002 33/530 |
| 7,083,824 B2 | * | 8/2006 | Stankowski | F01D 5/00 427/142 |
| 7,147,899 B2 | * | 12/2006 | Fernihough | C23C 14/042 427/154 |
| 7,302,990 B2 | * | 12/2007 | Bunker | B22C 9/10 164/138 |
| 7,329,832 B2 | | 2/2008 | Hoebel et al. | |
| 7,333,218 B2 | | 2/2008 | Vaidyanathan | |
| 7,351,290 B2 | * | 4/2008 | Rutkowski | B05C 5/0216 118/683 |
| 7,388,980 B2 | | 6/2008 | Vaidyanathan | |
| 7,574,035 B2 | | 8/2009 | Koonankeil | |

(Continued)

*Primary Examiner* — Freddie Kirkland, III
(74) *Attorney, Agent, or Firm* — Armstrong Teasdale LLP

(57) ABSTRACT

A system for locating at least one surface feature, such as a cooling aperture, on a turbine component is provided. The system includes at least one feature marker configured for placement adjacent to the at least one surface feature. The system also includes at least one sensor configured for non-visual detection of the at least one feature marker. The system also includes a control device coupled to the at least one sensor for receiving signals from the at least one sensor, wherein the signals represent data indicative of one of a presence of the at least one feature marker and an absence of the at least one feature marker.

20 Claims, 5 Drawing Sheets

(56) References Cited

U.S. PATENT DOCUMENTS

| | | | |
|---|---|---|---|
| 7,725,210 B2 | 5/2010 | Hoebel et al. | |
| 7,762,004 B2 * | 7/2010 | Sherlock | F01D 25/285 33/562 |
| 8,218,001 B2 | 7/2012 | Hastilow | |
| 8,365,584 B1 * | 2/2013 | Quinones | G01N 29/225 73/112.05 |
| 8,640,531 B2 * | 2/2014 | Remillard | F01D 21/003 73/112.01 |
| 9,103,801 B2 * | 8/2015 | Hirano | G01N 27/9006 |
| 9,151,587 B2 * | 10/2015 | Ward, Jr. | F01D 25/285 |
| 2005/0191422 A1 * | 9/2005 | Fernihough | C23C 14/042 427/282 |
| 2005/0217131 A1 * | 10/2005 | Varsell | G01B 3/14 33/562 |
| 2006/0022666 A1 | 2/2006 | Hughes | |
| 2007/0241084 A1 * | 10/2007 | Hoebel | F01D 5/005 219/121.71 |
| 2008/0048635 A1 | 2/2008 | Hughes | |
| 2011/0218741 A1 * | 9/2011 | Hirano | G01N 27/9006 702/38 |
| 2015/0158044 A1 * | 6/2015 | Reid | B05B 12/02 427/8 |
| 2015/0219451 A1 * | 8/2015 | Pettersson | G01B 5/008 33/503 |

\* cited by examiner

METHOD AND SYSTEM FOR DETECTING SURFACE FEATURES ON TURBINE COMPONENTS

BACKGROUND

The present disclosure relates to turbomachinery, and, more specifically, to methods and systems for detecting and locating turbine component surface features, such as cooling apertures, during repair of turbine components.

At least some known turbomachines, such as gas turbines, include surface features such as cooling air apertures that are defined on surfaces of turbine nozzles, rotor blade airfoils, and/or shrouds. Turbine nozzles, rotor blade airfoils, and/or shrouds typically include a substrate over which a coating is applied. During fabrication, after the coating has been applied, surface features such as cooling apertures are defined, for example by drilling through the coating and into, and/or through, the substrate. When a turbine component is repaired, the coating is removed. Cooling apertures previously drilled into the substrate remain after the substrate has been repaired. However, challenges may be presented when a stripped turbine component is being repaired and recoated with a corrosion and/or heat-resistant coating, wherein subsequent recoating of the turbine component may undesirably obscure surface features located on the turbine component. Restoration of cooling apertures to their original geometries, and removal of any excess coating debris obstructing or blocking the cooling apertures, are important to a successful and complete repair of the turbine component.

At least some known repair methods involve visually scanning a component, after the coating has been removed, to record locations of cooling apertures as a set of data points. After the coating has been reapplied, cooling apertures that have been obscured and/or covered over by the coating are cleared via a clearing device. The clearing device may be a device such as, but not limited to, a laser, a water jet, an electrical discharge machining device ("EDM"), an electrochemical machining ("ECM") device, a mechanical removal device (such as, but not limited to, a drill or reamer), an ultrasonic device, and/or a grit blasting device, coupled to a robotic arm or similar device. The movements of the robotic arm are controlled by a programmable controller that relies upon the previously-recorded data points to precisely position the clearing device. Without a verified initial starting point, however, the programmable controller may not be able to position the clearing device with sufficient precision to clear the cooling apertures without removing more of the reapplied coating than is necessary to clear the cooling apertures.

As an alternative, at least some repair methods may involve the placement of elongated plugs in the cooling apertures prior to reapplication of the coating layers, such that the plugs extend above the reapplied coating layers to indicate the locations of the cooling apertures. However, such elongated plugs may interfere with the reapplication of the coating. Moreover, because of the number of cooling apertures that may be present on a single turbine component, placing a plug in each cooling aperture may represent a time-consuming effort.

BRIEF DESCRIPTION

In one aspect, a method for locating at least one surface feature on a turbine component, wherein the at least one surface feature at least partially penetrates a surface of the turbine component, is provided. The method includes positioning at least one feature marker adjacent to the at least one surface feature. The method also includes detecting via non-visual sensing a location of the at least one feature marker.

In another aspect, a system for locating at least one surface feature on a turbine component, wherein the at least one surface feature at least partially penetrates a surface of the turbine component, is provided. The system includes at least one feature marker configured for placement adjacent to the at least one surface feature on the turbine component. The system also includes at least one sensor configured for non-visual detection of the at least one feature marker. The system also includes a control device coupled to the at least one sensor for receiving signals from the at least one sensor, wherein the signals represent data indicative of one of a presence of the at least one feature marker and an absence of the at least one feature marker.

DETAILED DESCRIPTION

As used herein, the terms "axial" and "axially" refer to directions and orientations extending substantially parallel to a longitudinal axis of a turbomachine. Moreover, the terms "radial" and "radially" refer to directions and orientations extending substantially perpendicularly to the longitudinal axis of the turbomachine. In addition, as used herein, the terms "circumferential" and "circumferentially" refer to directions and orientations extending arcuately about the longitudinal axis of the turbomachine. It should also be appreciated that the term "fluid" as used herein includes any medium or material that flows, including, but not limited to, gas and air. As used herein, the term "turbine component" refers to any structure within a turbomachine that includes surface features that may be obscured and/or blocked by coating material during reapplication of a coating following repair of the structure.

Figure 1:
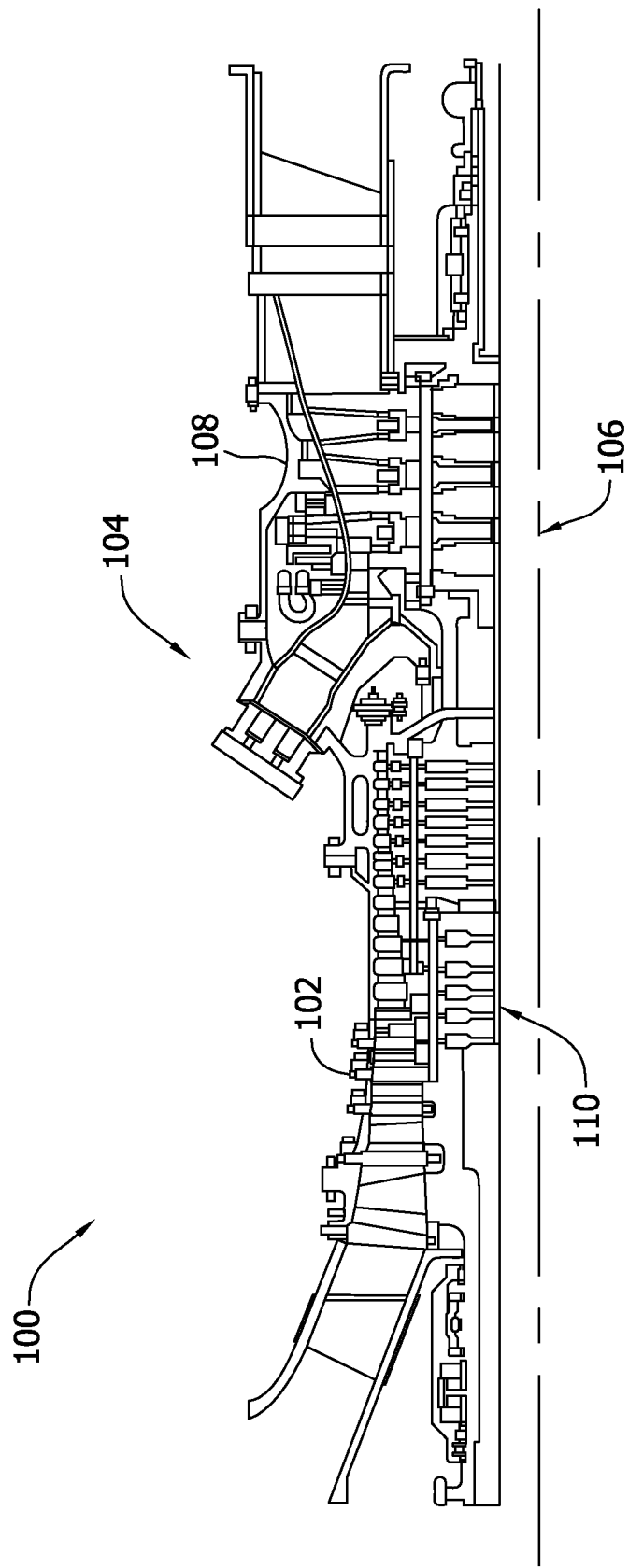
FIG. 1 is a schematic illustration of an exemplary gas turbine engine.

FIG. 1 is a schematic illustration of an exemplary gas turbine engine 100. Engine 100 includes a compressor assembly 102 and a combustor assembly 104. Engine 100 also includes a turbine 108 and a common compressor/turbine shaft or rotor 110. In operation, air flows through compressor assembly 102 such that compressed air is supplied to combustor assembly 104. Fuel is channeled to a combustion region and/or zone (not shown) that is defined within combustor assembly 104 wherein the fuel is mixed with the air and ignited. Resulting combustion gases are channeled to turbine 108, wherein gas stream thermal energy is converted to mechanical rotational energy. Turbine 108 is coupled to rotor 110, for rotation about an axis 106.

Figure 2:
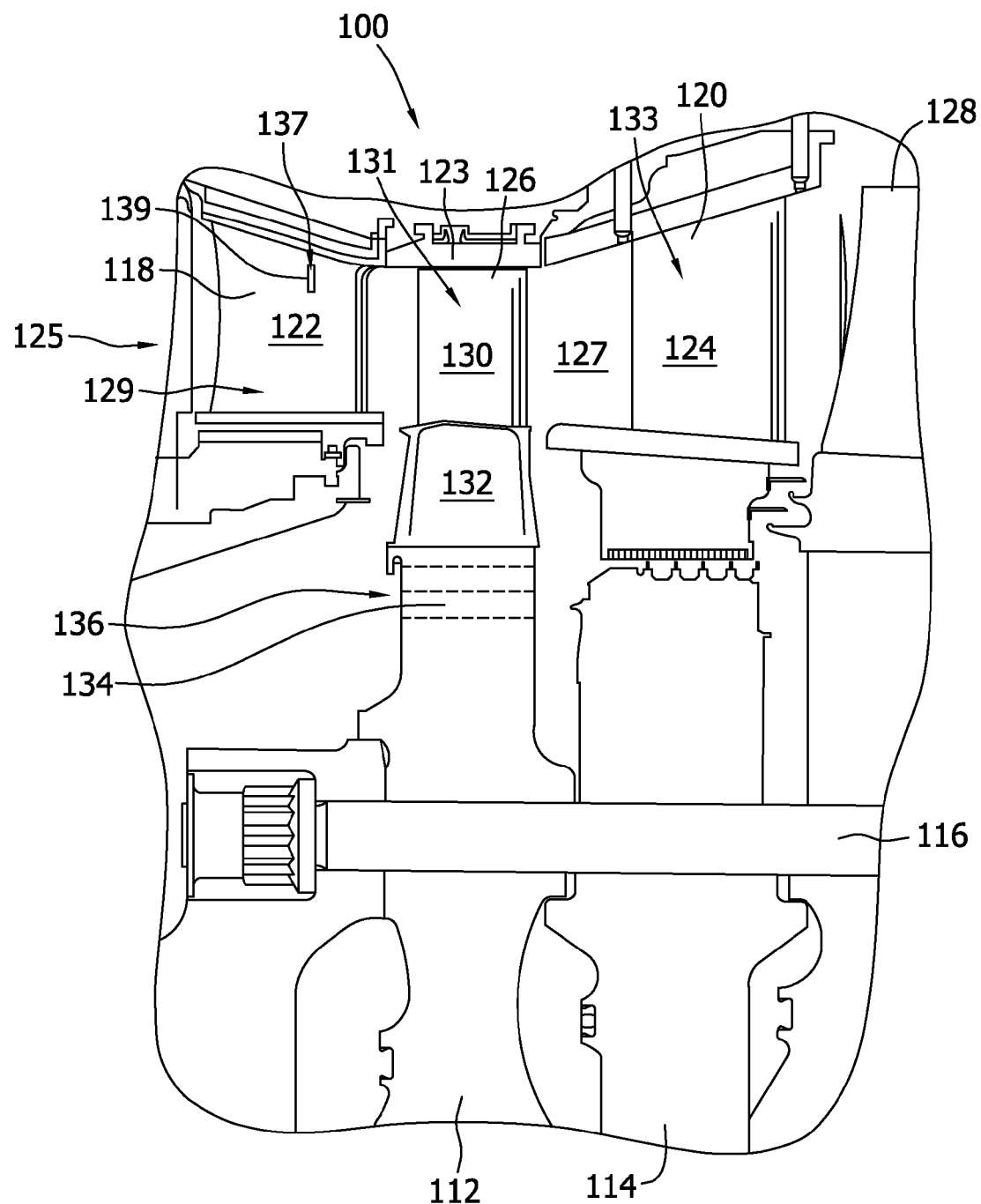
FIG. 2 is a side sectional view of a portion of the gas turbine engine shown in FIG. 1.

FIG. 2 is an enlarged schematic illustration of a portion of gas turbine engine 100 that includes axially spaced apart rotor disks 112 and spacers 114 that are coupled to each other, for example, by a plurality of circumferentially-spaced, axially-extending bolts 116. Although bolts 116 are illustrated in FIG. 2 for use in coupling disks 112 to spacers 114, any other suitable coupling structures may be used that enable gas turbine engine 100 to function as described herein. Gas turbine engine 100 includes, for example, a plurality of first-stage nozzles 118 and a plurality of second-stage nozzles 120. Each plurality of nozzles 118 and 120 includes a plurality of circumferentially-spaced stator vanes, such as stator vanes 122 and 124. A plurality of first-stage rotor blades 126 are coupled, for example, via disk 112, to rotor 110 (shown in FIG. 1), for rotation between nozzles 118 and 120. In the exemplary embodiment, each rotor blade 126 includes an airfoil 130 coupled to a shank 132. Similarly, a plurality of second-stage rotor blades 128 likewise is coupled to rotor 110, for rotation between second-stage nozzles 120 and a third stage of nozzles (not shown). Although two stages of rotor blades 126 and 128, and two stages of nozzles 118 and 120, are shown and described herein, at least some known gas turbine engines may include different numbers of nozzle and rotor blade stages.

Each rotor blade 126 is coupled to rotor disk 112 using any suitable coupling method that enables gas turbine engine 100 to function as described herein. Specifically, in the exemplary embodiment, each rotor blade 126 includes a dovetail 134 coupled to shank 132. Dovetail 134 is inserted axially (i.e., in a direction substantially parallel to axis of rotation 106 illustrated in FIG. 1) within a suitably-shaped slot 136 defined in rotor disk 112. In an example gas turbine engine 100, a flow 125 of hot combustion gases is channeled through rotor/stator cavity 127, exposing outer surfaces 129, 131, and 133, of stator vane 122, airfoil 130, stator vane 124, or a shroud 123, respectively, to high temperatures and potential corresponding thermal stresses and/or thermal degradation. To at least partially address such exposure, at least one of stator vane 122, airfoil 130, stator vane 124 and/or shroud 123 and/or any other hot component in the turbine are provided with a cooling system 137 that includes a cooling air supply channel (not shown) coupled to at least one subsurface passage (not shown) that terminates, for example, in at least one discharge aperture 139 in surface 129 of stator vane 122. Although air is specifically described, in alternative embodiments a fluid other than air may be used to cool components exposed to combustion gases. It should also be appreciated that the term "fluid" as used herein includes any medium or material that flows, including, but not limited to, gas, steam, and air.

Figure 3:
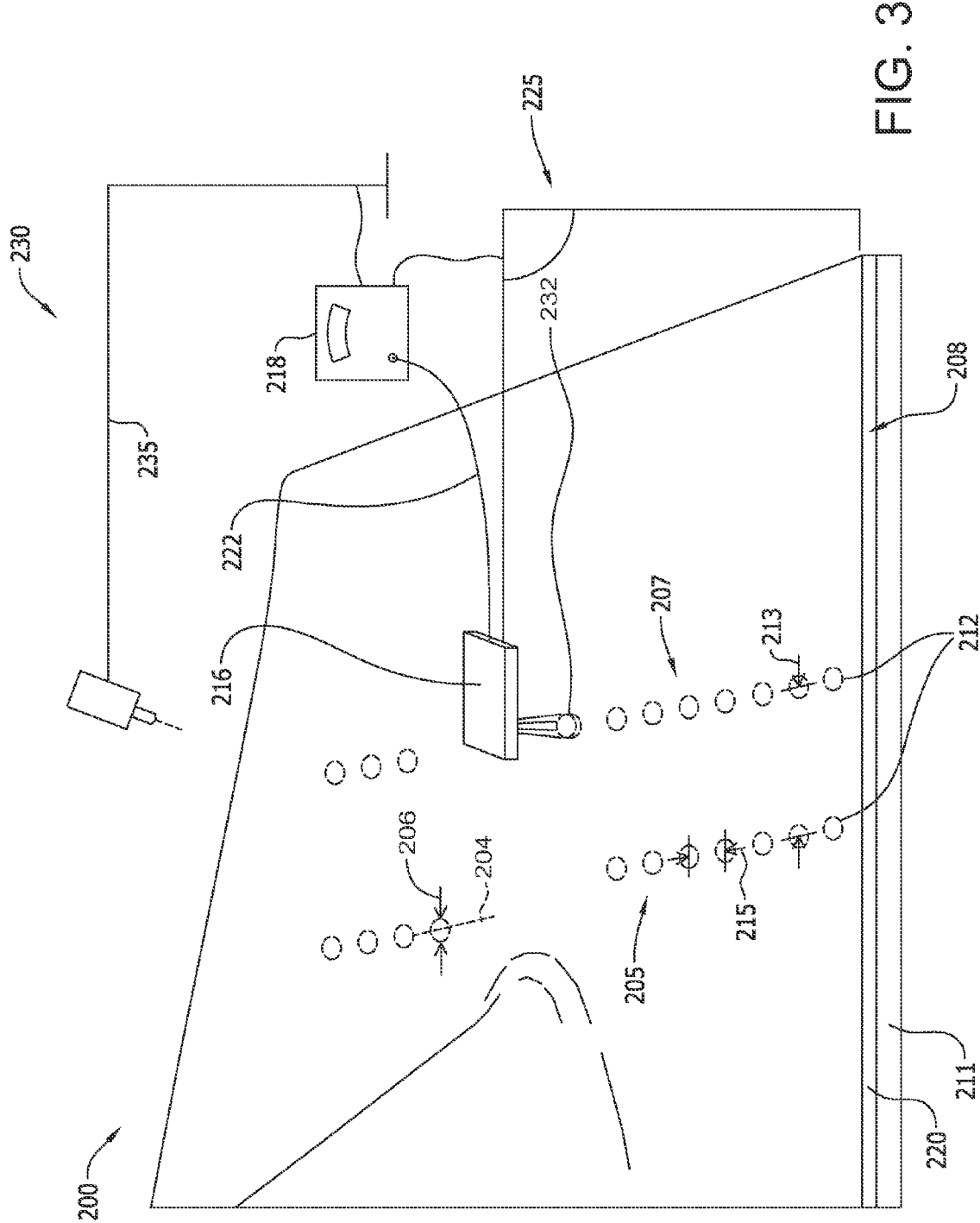
FIG. 3 is a perspective view of an exemplary surface feature locating system.

FIG. 3 is a perspective view of a feature detection system 230 for detecting features in a turbine component 200. In the exemplary embodiment, turbine component 200 may be a turbine nozzle, similar to nozzle 118 shown in FIG. 2. Nozzle 200 includes a plurality of cooling apertures 212 defined in a surface 208 thereof. In the exemplary embodiment, nozzle 200 may be fabricated from at least one non-magnetic material. Moreover, in the exemplary embodiment, apertures 212 each have a substantially uniform diameter 206. In addition, apertures 212 are circular when viewed along a direction of a center axis 204. In addition, apertures 212 are separated by predefined and recorded distances 215, which may or may not be uniform. Similarly, rows 205 and 207 of apertures 212 are separated by predefined and recorded distances 213, which may or may not be uniform.

As illustrated in FIG. 3, in the exemplary embodiment, nozzle 200 has been repaired, and has been recoated with a ceramic and/or heat-resistant coating 220. Repaired nozzle 200 includes a base layer 211 to which coating 220 is applied. Base layer 211 is typically fabricated from a nickel-based, non-magnetic, but magnetically permeable, material. In the exemplary embodiment, coating 220 includes at least one layer of material, such as a ceramic material. As previously described, recoating a stripped and repaired turbine component may present challenges, as the reapplied coating may obscure apertures 212. In the exemplary embodiment, feature detection system 230 includes at least one feature marker 232. Prior to reapplication of coating 220, at least one feature marker 232 is inserted into a corresponding aperture 212. In the exemplary embodiment, feature marker 232 is fabricated from a magnetic material. In an alternative embodiment, feature marker 232 may be fabricated from any suitable material that enables the detection methods described herein to be performed as described.

In the exemplary embodiment, system 230 also includes at least one sensor 216 coupled via a connector 222 to a control device 218. Connector 222 channels data signals transmitted from sensor 216 to control device 218, and also channels control signals transmitted from control device 218 to sensor 216. In the exemplary embodiment, sensor 216 may have any configuration that enables system 230 to function as described herein. For example, sensor 216 may include an array (not shown) of at least two sensor units. The array may include, for example, at least one sensor unit configured for broad area scanning and at least one sensor unit configured for fine scale (i.e., small area) scanning.

In the exemplary embodiment, distances 213 between rows 205 and 207, and distances 215 between individual cooling apertures 212 are determined and recorded at the time of fabrication of nozzle 200, and subsequently stored in or accessible by control device 218. In addition, apertures 212 may also define a layout (which may or may not include a regularly-defined pattern) that is also determined and recorded at the time of fabrication of nozzle 200. In the exemplary embodiment, data associated with inter-row distances 213, data associated with inter-aperture distances 215, and data associated with details of any patterns formed by apertures 212 are collectively referred to herein as "spacing data." However, the position of any individual cooling aperture 212 with respect to the overall structure of nozzle 200 may vary slightly from component to component during initial fabrication of nozzle 200, for example because of variations in placement of nozzle 200 in a fixture (not shown) prior to drilling of cooling apertures 212.

In the exemplary embodiment, sensor 216 is any device, including, but not limited to, a Hall Effect sensor, that may be used to detect the presence of a structure that emits a magnetic field, such as feature marker 232. In the exemplary embodiment, sensor 216 is coupled to a location sensing device 225 that is coupled to control device 218. More particularly, location sensing device 225 may be a coordinate-measuring machine ("CMM"). Location sensing device 225 enables a location of sensor 216, relative to nozzle 200, to be determined and recorded with any desired level of precision that enables system 230 to function as described herein.

In the exemplary embodiment, a method for implementing system 230 to locate apertures 212 on nozzle 200 is initiated with the removal of coating 220 prior to repair of nozzle 200. After base layer 211 of nozzle 200 has been repaired, and before reapplication of coating 220, feature markers 232 are positioned within a predefined number, and less than all, of apertures 212 in at least one of rows 205, 207. In the exemplary embodiment, feature markers 232 are positioned in apertures 212 at the ends of a row 205 and/or 207. In alternative embodiments, feature markers 232 may be positioned at any locations on nozzle 200 that enable system 230 to function as described herein. Coating 220 is then reapplied to nozzle 200. Each feature marker 232 is located by moving sensor 216 over nozzle 200 until control device 218 indicates the presence of a magnetic field corresponding to a feature marker 232. A location of each detected feature marker 232 relative to nozzle 200 is determined using location sensing device 225 and recorded by control device 218. After all feature markers 232 have been located and their locations have been recorded, the locations of remaining apertures 212 relative to the overall structure of nozzle 200 can be determined by control device 218 via interpolation using the previously-determined spacing data. In the exemplary embodiment, the locations of feature markers 232 may be determined at any time during the process of repairing nozzle 200 that enables system 230 to function as described herein. For example, in alternative embodiments, the locations of feature markers 232 may be obtained prior to reapplication of coating 220, between applications of separate layers (not shown) of coating 220, or after completion of reapplication of coating 220. Moreover, in still another alternative embodiment, feature markers 232 may be placed in predefined apertures 212 during initial fabrication of nozzle 200, such that the locations of feature markers 232 may be determined and recorded prior to removal of coating 220.

As previously described, in the exemplary embodiment, feature markers 232 are fabricated from a magnetic material. In an alternative embodiment, feature markers 232 are fabricated from a non-magnetic, but magnetically permeable material, such as a ferro-magnetic material, including, but not limited to, steel. Specifically, the magnetic permeability of feature marker 232, for example, may be different from a magnetic permeability of the material from which nozzle 200 is fabricated. Accordingly, instead of directly detecting a magnetic field emanating from feature marker 232, sensor 216 is configured to detect changes in magnetic permeability as sensor 216 is moved over nozzle 200.

Figure 4:
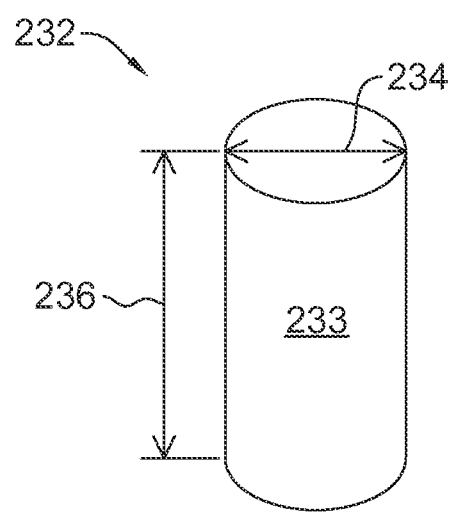
FIG. 4 is a perspective view of an exemplary feature marker that may be used in the feature locating system shown in FIG. 3.

Instead of prefabricated feature markers 232 shown in FIGS. 3-4, in alternative embodiments (not shown), system 230 may include at least one non-prefabricated feature marker. A non-prefabricated feature marker may be configured as a malleable, amorphous body that is placed over or within an aperture 212 prior to reapplication of coating 220. The amorphous body can have a magnetic field induced and temporarily retained within it, for example, via induction. Moreover, the amorphous body may be magnetized at any point in time during the repair of nozzle 200 that enables system 230 to function as described herein. The amorphous body may also be re-magnetized if necessary, as exposure to heat during application of coating 220 may cause de-magnetization of at least some known magnetizable materials. The amorphous body may be fabricated from a magnetic or magnetically permeable powder, or a paste or putty created by mixing the powder with a binder material. The powder, paste or putty may be placed within or over at least one of apertures 212 as necessary to enable system 230 to function as described herein.

Completion of a repair of nozzle 200 includes the removal of feature markers 232, either before or after reapplication of coating 220, followed by clearing of apertures 212. Clearing of apertures 212 is accomplished via a clearing device 235, the movements of which are controlled by control device 218, using the previously-determined locations of feature markers 232 and determining via interpolation, the locations of apertures 212 using the previously-determined spacing data. In the exemplary embodiment, clearing device 235 may be any device, including but not limited to, a laser, a water jet, an electrical discharge machining device ("EDM"), an electro-chemical machining ("ECM") device, a mechanical removal device (such as, but not limited to, a drill or reamer), an ultrasonic device, and/or a grit blasting device, and/or a grit blasting device, that is capable of removing coating layer material from nozzle 200 in a controlled manner. In general, clearing device 235 may be any material removal device that enables system 230 to function as described herein.

In the exemplary embodiment, the method of removal of feature markers 232 depends on the type of feature marker 232 that was used, and at what point during the process of repairing nozzle 200 that feature markers 232 are removed. For example, if the feature markers 232 that are used are the prefabricated type, they may be pried out of nozzle 200 using any removal method that enables system 230 to function as described herein. If the feature markers 232 that are used are of the non-prefabricated type, and removal is performed prior to reapplication of coating 220, feature markers 232 may be removed using a magnet (not shown). Alternatively, if feature markers 232 that are used are of the non-prefabricated amorphous body type, and removal is performed subsequent to reapplication of coating 220, feature markers 232 may be removed using any suitable method, including using clearing device 235. If desired, the process of location of feature markers 232 may be performed multiple times during a repair of nozzle 200, prior to removal of feature markers 232.

As previously described, in the exemplary embodiment, feature markers 232 are fabricated from a material that is permanently magnetized or which can have a magnetic field induced therein. In an alternative embodiment, feature markers 232 may be fabricated from any material that facilitates non-visual detection through a layer of coating material. For example, feature markers 232 may be fabricated from a material that simply has different magnetic or electrical properties than base layer 211 or coating 220. Accordingly, sensor 216 may have any configuration that can detect the presence of a feature marker 232, through a coating 220, if present. For example, in an alternative embodiment wherein feature marker 232 is a magnet, system 230 may include a sensor 216 in the form of a permanent magnet or electromagnet supported by location sensing device 225. Upon encountering a feature marker 232, sensor 216 is attracted toward or repulsed away from feature marker 232, such that the location of feature marker 232 may be sensed by location sensing device 225 and recorded by control device 218.

In another alternative embodiment, wherein feature markers 232 are permanent magnets, sensor 216 may be configured as an electromagnetic sensor, such, but not limited to, an electric coil (not shown) to which an A.C. current is supplied by control device 218. In this embodiment, control device 218 is configured to detect eddy currents sensed by sensor 216. The use of eddy currents to detect feature markers 232 facilitates the use of a CMM device or other robotic device as location sensing device 225, as the detection of feature markers 232 via eddy currents does not involve the imposition of physical loads (e.g., via magnetic attraction/repulsion) on location sensing device 225. In this embodiment, sensor 216 may be configured as an eddy current pencil probe sensor. The use of an electric coil, such as an eddy current pencil probe sensor, in sensor 216 facilitates the conversion of signals received from sensor 216 into digital data, for example, via an analog-to-digital (A/D) converter (not shown) within control device 218. Digital data obtained in this manner may be converted into a visual representation (not shown) presented on a display device such as a media output device 315 associated with control device 218. Inspection of the visual representation may readily reveal a maximum induced response or other signal feature representative of a location of a feature marker 232, facilitating a determination of an aperture 212 associated with the feature marker 232. Alternatively, sensor 216 may have any suitable configuration that enables system 230 to function as described herein.

FIG. 4 is a perspective view of an exemplary feature marker 232 that may be used in system 230 (shown in FIG. 3). In the exemplary embodiment, feature marker 232 includes a cylindrical body 233, having a diameter 234 that is smaller than diameter 206 (shown in FIG. 3) of apertures 212, but is sufficiently close to diameter 206 to ensure that a slight friction fit is created between marker 232 and aperture 212. Feature marker 232 has a height 236. In the exemplary embodiment, height 236 is any length that enables feature marker 232 to function as described herein. For example, in one embodiment, height 236 may be larger than diameter 234. In an alternative embodiment, height 236 may be smaller than diameter 234. In yet another alternative embodiment, height 236 may be approximately equal to diameter 234.

In an alternative embodiment (not shown), feature marker 232 includes a frusto-conical body, having a first diameter that is smaller than diameter 206 (shown in FIG. 3) of apertures 212, and a second diameter that is larger than diameter 206. Accordingly, frusto-conical feature marker 232 may fit into an aperture 212 with an interference fit such that at least a portion of a frusto-conical feature marker 232 remains above surface 208 after the frusto-conical feature marker 232 has been inserted into an aperture 212. In yet another alternative embodiment (not shown), feature marker 232 includes a cylindrical or disk-shaped head and a cylindrical post extending from the head, wherein the head has a larger diameter than the post, such that the feature marker 232 has a "T"-shaped cross-sectional configuration. In this alternative embodiment, the head will have a diameter that is larger than diameter 206, to prevent over-insertion of the "T"-shaped feature marker 232 into an aperture 212. The post will have a diameter that is smaller than diameter 206. In addition, the head may have any thickness that enables system 230 to function as described herein.

Figure 5:
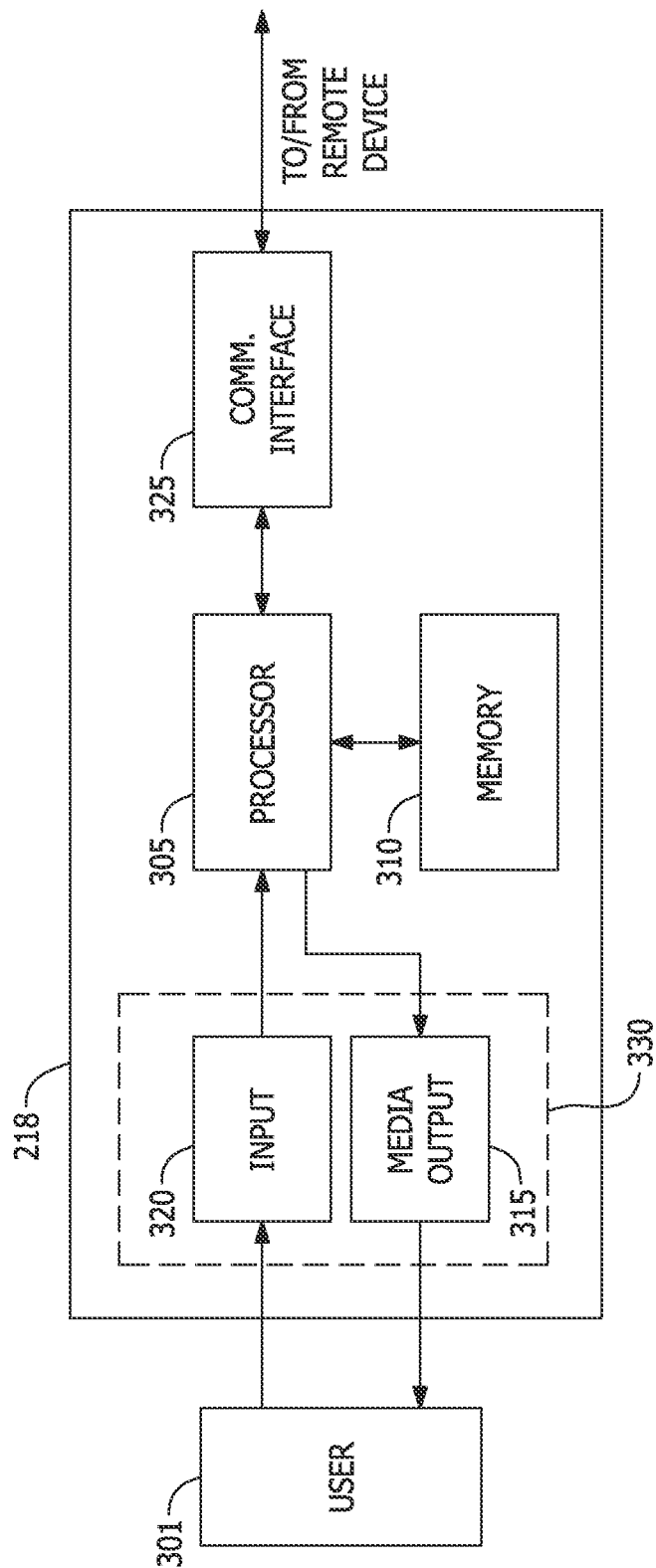
FIG. 5 is a block diagram of an exemplary control device configuration that may be used with the surface feature locating system shown in FIG. 3.

FIG. 5 is a block diagram of an exemplary control device 218. Control device 218 includes a processor 305 for executing instructions. In some embodiments, executable instructions are stored in a memory device 310. Processor 305 may include at least one processing unit (e.g., in a multi-core configuration). Memory device 310 is any device allowing information such as executable instructions and/or other data to be stored and retrieved. Memory device 310 may include one or more computer-readable media.

In the exemplary embodiment, control device 218 also includes at least one media output device 315 for presenting information to a user 301. Media output device 315 is any component capable of conveying information to user 301. In some embodiments, media output device 315 is a video display. In some embodiments, media output device 315 includes an output adapter such as a video adapter and/or an audio adapter (not shown). An output adapter is operatively coupled to processor 305 and operatively coupleable to an output device such as a display device (e.g., a liquid crystal display (LCD), organic light emitting diode (OLED) display, cathode ray tube (CRT), or "electronic ink" display) or an audio output device (e.g., a speaker or headphones).

In some embodiments, control device 218 includes an input device 320 for receiving input from user 301. Input device 320 may include, for example, a keyboard, a pointing device, a mouse, a stylus, a touch sensitive panel (e.g., a touch pad or a touch screen), a gyroscope, an accelerometer, a position detector, or an audio input device. A single component such as a touch screen 330 may function as both an output device of media output device 315 and input device 320.

Control device 218 may also include a communication interface 325, which is communicatively coupleable to a remote device (not shown). Communication interface 325 may include, for example, a wired or wireless network adapter or a wireless data transceiver for use with a mobile phone network (e.g., Global System for Mobile communications (GSM), 3G, 4G or Bluetooth) or other mobile data network (e.g., Worldwide Interoperability for Microwave Access (WIMAX)).

Stored in memory device 310 are, for example, computer-readable instructions for providing a user interface to user 301 via media output device 315 and, optionally, receiving and processing input from input device 320. A user interface may include, among other possibilities, a web browser and client application. Web browsers enable users, such as user 301, to display and interact with media and other information typically embedded on a web page or a website from server system (not shown).

In the exemplary embodiment, control device 218 regulates functions of sensor 216 and processes signals received from sensor 216 via connector 222 into data regarding sensed locations of feature markers 232 relative to nozzle 200 as a whole. In the exemplary embodiment, control device 218 also controls the operations of location sensing device 225 and/or such that upon receipt of instructions from a user 301, control device 218 performs functions such as, but not limited to, (1) regulating movement of sensor 216 over nozzle 200; (2) sending control signals to sensor 216; (3) receiving sensor signals from sensor 216; (4) processing the received sensor signals from sensor 216 into location data regarding feature markers 232; (5) associating the location data with previously-determined spacing data stored, for example, in memory device 310; and/or (6) controlling operation of clearing device 235.

The term processor, as used herein, refers to central processing units, microprocessors, microcontrollers, reduced instruction set circuits (RISC), application specific integrated circuits (ASIC), logic circuits, and any other circuit or processor capable of executing the functions described herein.

As used herein, the terms "software" and "firmware" are interchangeable, and include any computer program stored in memory for execution by processor 305, including RAM memory, ROM memory, EPROM memory, EEPROM memory, and non-volatile RAM (NVRAM) memory. The above memory types are example only, and are thus not limiting as to the types of memory usable for storage of a computer program.

The methods and systems described herein enable surface features, such as cooling apertures that are defined on surfaces of turbine structures, including but not limited to turbine nozzles, rotor blades, and/or cooled shrouds, to be located and cleared during a repair procedure being performed on the turbine structure. The methods and systems described herein provide several advantages over known methods and systems of detecting surface features in gas turbine components. Specifically, the methods and systems described herein facilitate detection of surface features on turbine components without the use of visual inspection. More particularly, the methods and systems described herein facilitate detection of surface features on turbine components that are covered by a coating. The methods and systems described herein also enable the locations of surrounding surface features to be identified using predetermined spacing data regarding the surface features. The methods and systems described herein also enable the subsequent removal of coating material debris from obscured or blocked surface features, without requiring the detection and recording of the location of each surface feature on the turbine component prior to reapplication of the coating.

Exemplary embodiments of methods and systems for locating surface features in turbine components are described above in detail. The methods and systems are not limited to the specific embodiments described herein, but rather, actions of the methods and/or components of the systems may be utilized independently and separately from other components and/or actions described herein. For example, the methods and systems described herein are not limited to practice only with rotor blades and turbine nozzles, but also may be used in combination with other turbine components that incorporate surface features that may be obscured and/or blocked during reapplication of a coating following repair of the component. Moreover, the exemplary embodiment may be implemented and utilized in connection with many other rotary machine applications, other than gas turbines.

The methods and systems are not limited to the specific embodiments described herein, but rather, operations of the methods and/or components of the systems may be utilized independently and separately from other components and/or actions described herein. The method operations described herein are just examples. There may be many variations to the operations described therein without departing from the spirit of the disclosure. For instance, except as specifically described, the actions may be performed in a differing order, or actions may be added, deleted or modified. All of these variations are considered a part of the claimed subject matter of the disclosure.

Although specific features of various embodiments of the disclosure may be shown in some drawings and not in others, this is for convenience only. In accordance with the principles of the disclosure, any feature of a drawing may be referenced and/or claimed in combination with any feature of any other drawing.

This written description uses examples to disclose the methods and systems described herein, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

While the disclosure has been described in terms of various specific embodiments, those skilled in the art will recognize that the disclosure may be practiced with modification within the spirit and scope of the claims.

What is claimed is:

1. A method for locating at least one surface feature on a turbine component, wherein the surface feature at least partially penetrates a surface of the turbine component, said method comprising:
    positioning at least one feature marker adjacent to the at least one surface feature such that the at least one feature marker is removably coupled to the surface of the turbine component; and
    detecting via non-visual sensing a location of the at least one feature marker relative to the turbine component.

2. The method in accordance with claim 1, wherein said method comprises recording the sensed location of the at least one feature marker.

3. The method in accordance with claim 1, wherein said method comprises removing the at least one feature marker from the surface of the turbine component.

4. The method in accordance with claim 1, wherein the at least one feature marker includes a post insertable into the at least one surface feature and wherein positioning at least one feature marker adjacent to the at least one surface feature comprises inserting the feature marker into the at least one surface feature.

5. The method in accordance with claim 1, wherein the at least one feature marker is fabricated as a malleable, amorphous body and wherein positioning at least one feature marker adjacent to the at least one surface feature comprises at least one of inserting the malleable, amorphous body into the at least one surface feature and orienting the malleable, amorphous body over the at least one surface feature.

6. The method in accordance with claim 3, wherein removing the at least one feature marker comprises removing the at least one feature marker at a point in time which is one of prior to application of at least one coating layer to the turbine component and subsequent to application of the at least one coating layer to the turbine component.

7. The method in accordance with claim 1, wherein detecting a location of the at least one feature marker comprises sensing the at least one feature marker with an electromagnetic sensor.

8. The method in accordance with claim 1, wherein detecting a location of the at least one feature marker comprises sensing changes in magnetic permeability with a sensor as the sensor is moved over the turbine component.

9. The method in accordance with claim 1, wherein said method comprises identifying locations of other surface features in the turbine component via interpolation using spacing data representing predetermined positions of the other surface features relative to the at least one surface feature.

10. The method in accordance with claim 1, wherein said method comprises clearing coating material debris from the at least one surface feature.

11. The method in accordance with claim 10, wherein clearing coating material debris from the at least one surface feature comprises removing coating material debris with at least one of a laser, a water jet, an EDM device, an ECM device, a mechanical removal device, an ultrasonic device, and a grit blasting device.

12. A system for locating at least one surface feature on a turbine component, wherein said at least one surface feature at least partially penetrates a surface of the turbine component, said system comprising:
    at least one feature marker configured for placement adjacent to said at least one surface feature on the turbine component such that said at least one feature marker is removably coupled to the surface of the turbine component;
    at least one sensor configured for non-visual detection of a location of said at least one feature marker relative to the turbine component; and
    a control device coupled to said at least one sensor for receiving signals from said at least one sensor, wherein the signals represent data indicative of one of a presence of said at least one feature marker and an absence of said at least one feature marker.

13. The system in accordance with claim 12, wherein said system comprises a location sensing device coupled to said at least one sensor and to said control device.

14. The system in accordance with claim 12, wherein said system comprises a clearing device for removing coating material debris from said at least one surface feature after said at least one surface feature is located.

15. The system in accordance with claim 14, wherein said clearing device includes at least one of a laser, a water jet, an EDM device, an ECM device, a mechanical removal device, an ultrasonic device, and a grit blasting device.

16. The system in accordance with claim 12, wherein said at least one feature marker comprises a post, wherein said post includes a diameter that is smaller than the diameter of said at least one surface feature.

17. The system in accordance with claim 12, wherein said at least one feature marker comprises an amorphous body fabricated from a malleable material.

18. The system in accordance with claim 12, wherein said at least one feature marker comprises a permanent magnet, and wherein said at least one sensor is configured for sensing a magnetic field emanated by said at least one feature marker.

19. The system in accordance with claim 12, wherein said at least one feature marker comprises a first permanent magnet, and wherein said at least one sensor includes a second permanent magnet configured to be one of attracted by said first permanent magnet in said at least one feature marker, and repelled by said first permanent magnet in said at least one feature marker.

20. The system in accordance with claim 12, wherein said at least one feature marker includes a magnetically permeable material and wherein said at least one sensor comprises an electromagnetic probe.

\* \* \* \* \*